US005651491A

United States Patent [19]
Heaton et al.

[11] Patent Number: 5,651,491
[45] Date of Patent: Jul. 29, 1997

[54] SURGICAL STAPLER HAVING INTERCHANGEABLE LOADING UNITS

[75] Inventors: Lisa W. Heaton, Norwalk; Mitchell J. Palmer, New Milford; Wasim Munawar, West Haven; Robert C. Savage, Stratford; Robert J. Geiste, Milford, all of Conn.

[73] Assignee: United States Surgical Corporation, Norwalk, Conn.

[21] Appl. No.: 549,578

[22] Filed: Oct. 27, 1995

[51] Int. Cl.$^6$ .................................................. A61B 17/068
[52] U.S. Cl. .................................. 227/175.1; 227/176.1; 227/19
[58] Field of Search ........................... 227/19, 175.1, 227/176.1, 901

[56] References Cited

U.S. PATENT DOCUMENTS

| | | |
|---|---|---|
| Re. 34,519 | 1/1994 | Fox et al. . |
| 3,079,606 | 3/1963 | Bobrov et al. . |
| 3,275,211 | 9/1966 | Hirsch et al. . |
| 3,490,675 | 1/1970 | Green et al. . |
| 3,499,591 | 3/1970 | Green . |
| 4,108,306 | 8/1978 | Samuels et al. . |
| 4,354,628 | 10/1982 | Green . |
| 4,383,634 | 5/1983 | Green . |
| 4,429,695 | 2/1984 | Green . |
| 4,478,362 | 10/1984 | Foslien . |
| 4,506,670 | 3/1985 | Crossley . |
| 4,508,253 | 4/1985 | Green . |
| 4,520,817 | 6/1985 | Green . |
| 4,522,327 | 6/1985 | Korthoff et al. . |
| 4,527,724 | 7/1985 | Chow et al. . |
| 4,568,009 | 2/1986 | Green . |
| 4,573,622 | 3/1986 | Green et al. . |
| 4,585,153 | 4/1986 | Failla et al. . |
| 4,589,582 | 5/1986 | Bilotti . |
| 4,591,085 | 5/1986 | DiGiovanni . |
| 4,605,004 | 8/1986 | DiGiovanni et al. . |
| 4,606,344 | 8/1986 | DiGiovanni . |
| 4,606,345 | 8/1986 | Dorband et al. . |
| 4,607,636 | 8/1986 | Kula et al. . |
| 4,610,383 | 9/1986 | Rothfuss et al. . |
| 4,633,861 | 1/1987 | Chow et al. . |
| 4,633,874 | 1/1987 | Chow et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,809,898 | 3/1989 | Gassner et al. . |
| 4,819,853 | 4/1989 | Green . |
| 4,848,637 | 7/1989 | Pruitt . |
| 4,863,088 | 9/1989 | Redmond et al. . |

(List continued on next page.)

FOREIGN PATENT DOCUMENTS

| | | |
|---|---|---|
| 0136950 | 4/1985 | European Pat. Off. . |
| 0246870 | 11/1987 | European Pat. Off. . |
| 0674876 | 4/1995 | European Pat. Off. . |
| 0365153 | 8/1995 | European Pat. Off. . |
| 8302247 | 12/1982 | WIPO . |

*Primary Examiner*—Scott A. Smith

[57] ABSTRACT

A surgical stapler is disclosed which includes a first body portion supporting an anvil which defines a fastener forming surface and a second body portion configured to releasably mate with the first body portion and having an elongate retention channel extending from a distal end thereof. A first disposable loading unit is provided which is configured to be removably supported in the retention channel and which includes a staple housing carrying a plurality of staples arranged in at least two parallel rows which, when applied to body tissue, form staple lines having a first lengthwise dimension. A second disposable loading unit is provided which is configured to be removably supported in the retention channel and which includes a staple housing carrying a plurality of staples arranged in at least two parallel rows which, when applied to body tissue, form staple lines having a second lengthwise dimension different from that of the staple lines formed by the first loading unit. The loading units and stapler can be packaged as a kit.

23 Claims, 16 Drawing Sheets

U.S. PATENT DOCUMENTS

| | | |
|---|---|---|
| 4,881,544 | 11/1989 | Green et al. . |
| 4,881,545 | 11/1989 | Isaacs et al. . |
| 4,892,244 | 1/1990 | Fox et al. . |
| 4,915,100 | 4/1990 | Green . |
| 4,941,623 | 7/1990 | Pruitt . |
| 4,955,959 | 9/1990 | Tompkins et al. . |
| 5,031,814 | 7/1991 | Tompkins et al. . |
| 5,040,715 | 8/1991 | Green et al. . |
| 5,065,929 | 11/1991 | Schulze et al. . |
| 5,074,454 | 12/1991 | Peters . |
| 5,083,695 | 1/1992 | Foslien et al. . |
| 5,100,042 | 3/1992 | Gravener et al. . |
| 5,111,987 | 5/1992 | Moeinzadeh et al. . |
| 5,129,570 | 7/1992 | Schulze et al. . |
| 5,141,144 | 8/1992 | Foslien et al. . |
| 5,318,221 | 6/1994 | Green et al. . |
| 5,326,013 | 7/1994 | Green et al. . |
| 5,332,142 | 7/1994 | Robinson et al. . |
| 5,415,334 | 5/1995 | Williamson, IV et al. . |
| 5,415,335 | 5/1995 | Knodell, Jr. . |
| 5,447,265 | 9/1995 | Vidal et al. . |
| 5,470,006 | 11/1995 | Rodak . |
| 5,489,058 | 2/1996 | Plyley et al. ............... 227/19 |
| 5,535,934 | 7/1996 | Boiarski et al. ............ 227/19 |
| 5,547,711 | 8/1996 | Hamblin et al. ............ 227/19 |
| 5,551,622 | 9/1996 | Yoon ............................ 227/19 |

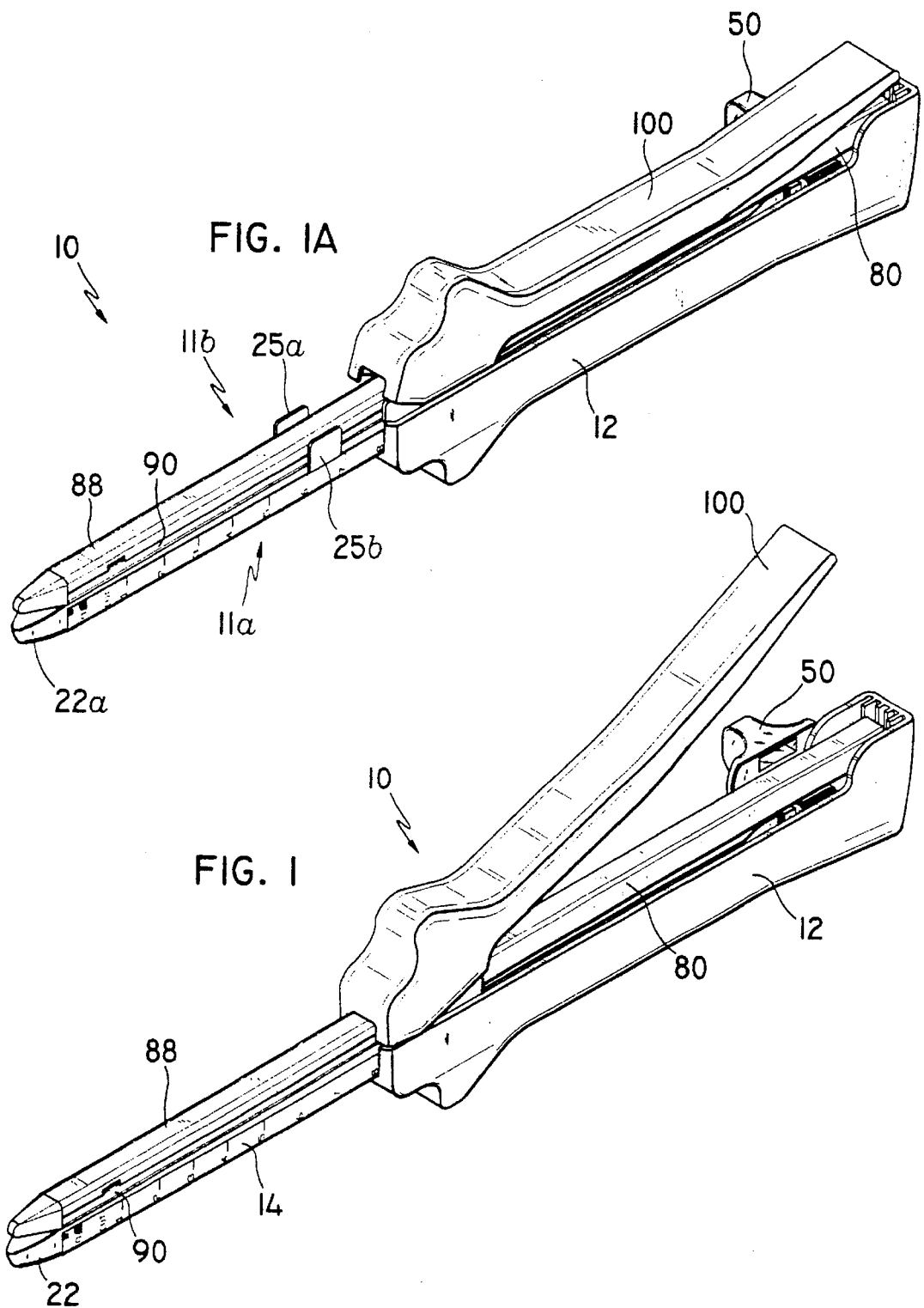

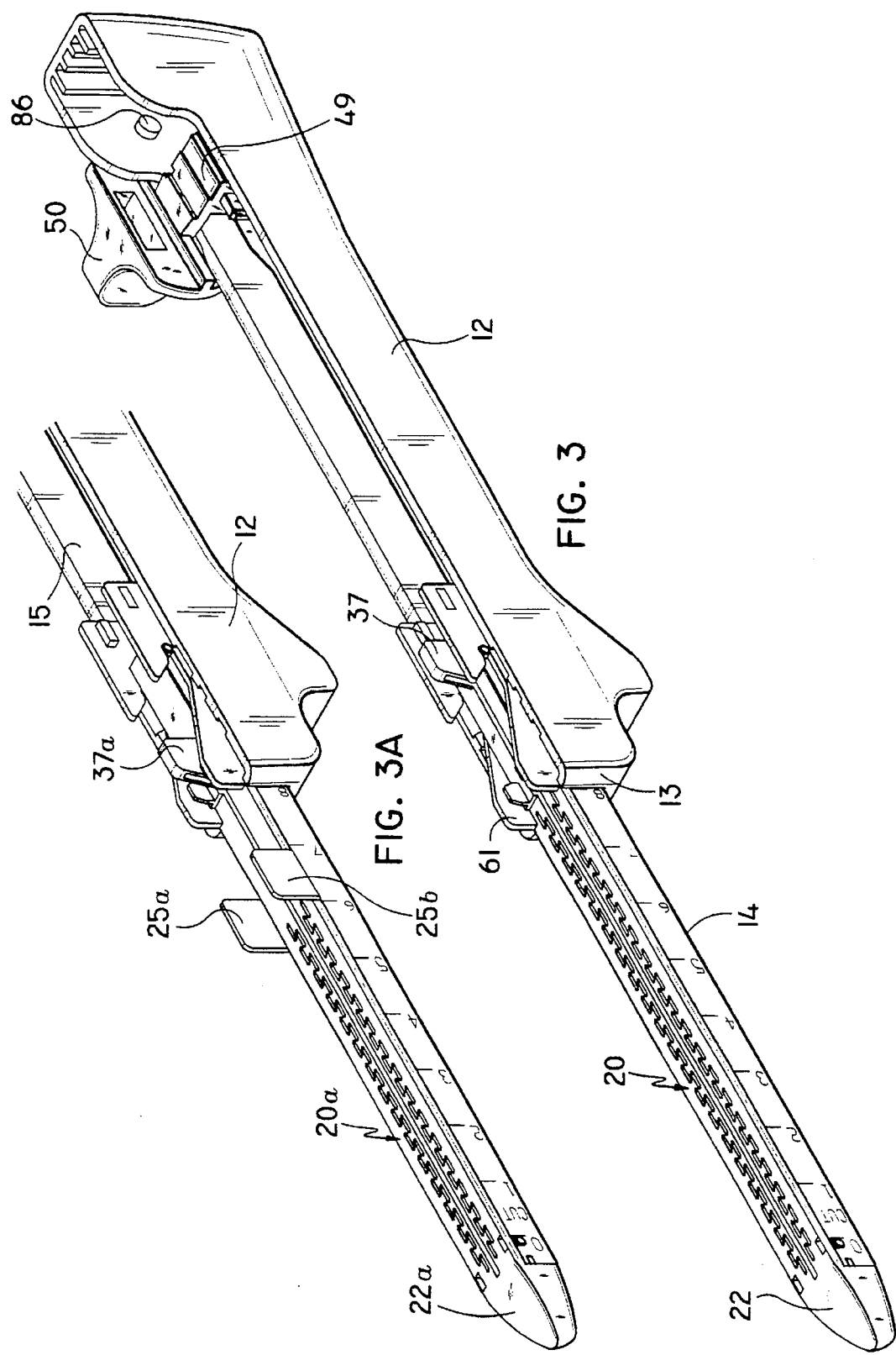

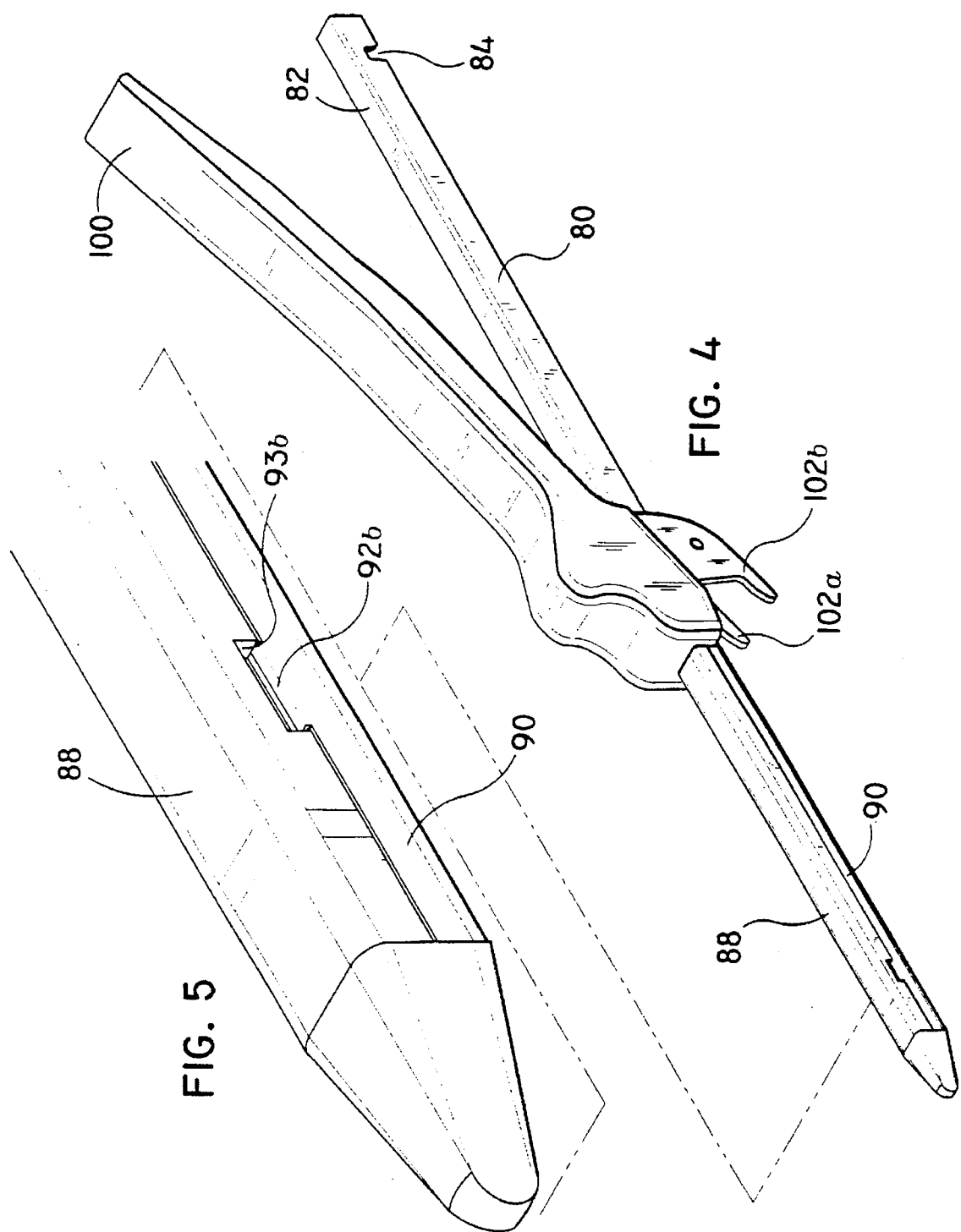

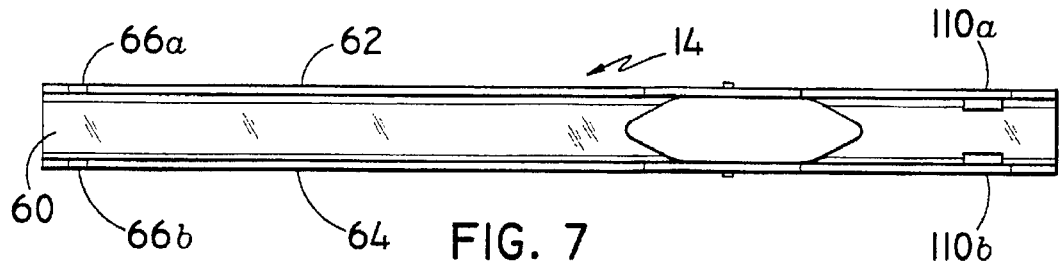
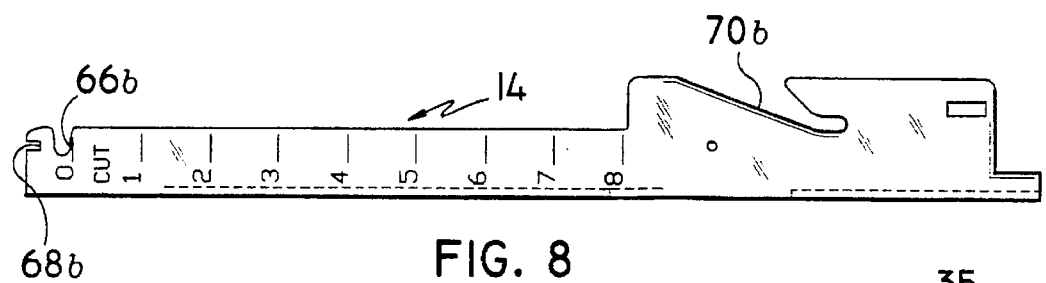
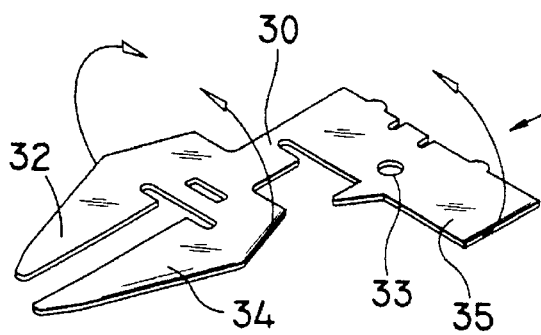
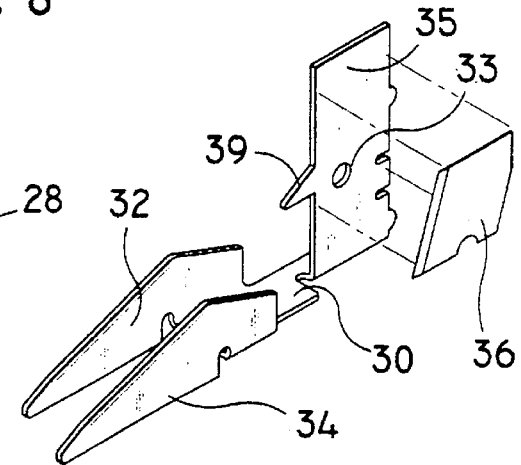
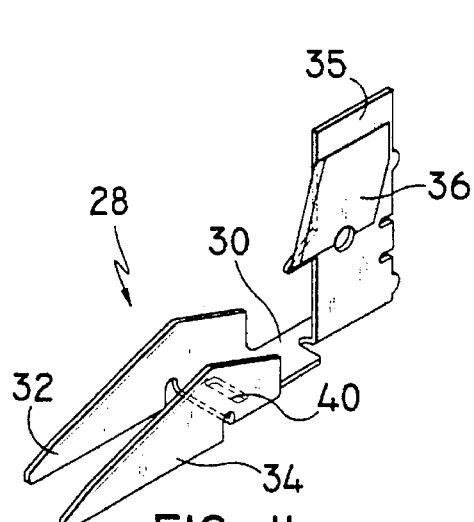
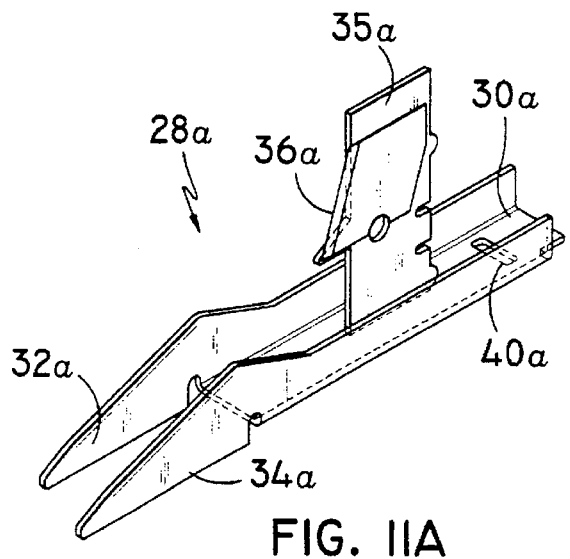

SURGICAL STAPLER HAVING INTERCHANGEABLE LOADING UNITS

BACKGROUND

1. Technical Field

This application relates to surgical staplers, and more particularly, to an apparatus for sequentially applying a plurality of surgical fasteners to body tissue.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of staples arranged in at least two lateral rows while the other member comprises an anvil which defines a surface for forming the staple legs as the fasteners are driven from the cartridge. Where two part fasteners are used, this member carries the mating part, e.g. the receiver, to the fastener driver from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. Nos. 3,079,606 and 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695, 5,065,929, and 5,156,614.

Many of the prior art linear stapling devices discussed above include a significant number of moving parts, small components and machined structural elements that are costly to fabricate and time consuming to assemble. These factors add to the overall cost of the stapling devices and thus increase the costs incurred by hospitals and health care professionals, and ultimately, the patient upon which the devices are utilized. It would be advantageous to provide a linear stapler that could be manufactured and assembled less expensively. It is also known that prior art linear stapling devices are specifically designed to apply staples rows of only one length. The linear staplers which are reloadable are configured to only receive a fresh array of staples of a fixed length. Thus, in surgical procedures requiring the placement of staple rows of varying length, it is necessary to employ different staplers, which, adds to the overall cost associated with the operation. It would be advantageous to provide a stapler which could be reloaded with varying length staple arrays to enable the application of staple rows of differing length to body tissue using a single stapler.

SUMMARY

The subject application is directed to a linear surgical stapler that is constructed from fewer, less expensive components than known prior art staplers configured to sequentially apply a plurality of surgical staples to body tissue. The stapler includes a first body portion supporting an anvil plate which defines a fastener forming surface and a second body portion configured to releasably mate with the first body portion. In the detailed description which follows, the first and second body portions of the stapler are also referred to as the "anvil half-section" and "cartridge half-section", respectively.

The stapler can removably support different disposable loading units. In particular, two disposable loading units are disclosed which are configured to be removably supported in the second body portion. Each loading unit includes a cartridge defining a plurality of slots and a tissue contacting surface, a plurality of surgical fasteners disposed in the slots, a plurality of ejectors or pushers positioned adjacent the surgical fasteners, and a wedged actuation sled configured to enter and translate through the cartridge to sequentially interact with the pushers. One of the loading units is adapted to apply parallel rows of staples each having a first lengthwise dimension, and the other loading unit is adapted to apply parallel rows of staple each having a second lengthwise dimension. Both loading units can be used with the stapler. The surgical stapler and differing disposable loading units can be packaged as a kit or the instrument and disposable loading units can be packaged separately.

The stapler in a preferred embodiment, includes an elongated actuation shaft mounted for longitudinal movement within the second body portion and releasably engagable with the wedged actuation sled of either loading unit, whereby longitudinal movement of the actuation shaft causes the wedged actuation sled to interact with the ejectors, driving the surgical fasteners from the cartridge to be formed against the anvil plate.

The first body portion preferably includes an elongated anvil support member and a pivoting lever handle. The anvil plate is preferably formed separate from the anvil support member and includes a plurality of staple forming pockets defining the anvil forming surface. The anvil plate also includes means for engaging the anvil support member during assembly of the surgical stapler to securely fasten the anvil plate to the support member. A notched area is defined adjacent a proximal end of the anvil support member and correspondingly positioned detents are formed adjacent a proximal end of the second body portion. The notched area and the detents cooperate to facilitate relative pivotal movement of the first and second body portions when they are mated with one another.

Preferably, a pair of upstanding flanges are formed on the disposable loading unit proximal of the tissue contacting surface thereof. The flanges are also dimensioned to engage a pair of corresponding apertures formed in the anvil plate to maintain the first and second body portions in alignment with one another when the surgical stapler is in a closed or damped position.

The wedged actuation sled is preferably monolithically formed from a planar piece of sheet metal during a stamping process and includes a planar base and a pair of upstanding parallel cam wedges. An upturned flange is formed at a distal end of the actuation member for releasably engaging a complementary slot formed in the base of the wedged actuator. The actuation sled further includes an upstanding support flange to which a knife blade is fastened. The knife blade is provided to form an incision in the stapled body tissue.

A retaining channel depends from a distal end of the second body portion for supporting either of the two disposable loading units. Preferably, both disposable loading units and the retaining channel include complementary engagement structures for releasably securing the disposable loading units in the retaining channel. Opposed bearing structures are formed in the retaining channel adjacent a proximal end thereof for abutting the anvil support beam when body tissue is clamped between the anvil plate and the tissue contacting surface of the cartridge. The bearing structures serve to inhibit the anvil support beam from bending as a result of the compressive forces generated during clamping.

Further features of the surgical apparatus of the subject application will become more readily apparent to those skilled in the art from the following detailed description of the apparatus taken in conjunction with the drawings.

BRIEF DESCRIPTION OF THE DRAWINGS

Various embodiments of the surgical stapling apparatus of the subject application will be described hereinbelow with reference to the drawings wherein:

FIG. 1 is a perspective view of a surgical stapling apparatus constructed in accordance with a preferred embodiment with the clamping handle thereof disposed in an upright open position and containing a disposable loading unit for applying a plurality of staple rows each having a first length;

FIG. 1A is a perspective view of the surgical stapling apparatus illustrated in FIG. 1 with the clamping handle disposed in a closed position and containing a disposable loading unit for applying a plurality of staple rows each having a second length;

FIG. 3 is a perspective view of the lower body portion of the surgical stapling apparatus and disposable loading unit of FIG. 1;

FIG. 3A is a perspective view of the lower body portion of the surgical stapling apparatus and disposable loading unit of FIG. 1A;

FIG. 4 is a perspective view of the upper body portion of the surgical stapling apparatus of FIGS. 1 and 1A;

FIG. 5 is an enlarged localized view of a distal portion of the upper body portion illustrating the connective engagement between the anvil plate and the anvil support beam;

FIG. 7 is a top plan view of the retention channel of the surgical stapling apparatus of FIGS. 1 and 1A;

FIG. 8 is a side elevational view of the retention channel shown in FIG. 7;

FIG. 9 is a perspective view of the actuation sled of the disposable loading unit shown in FIG. 6 in a pre-formed condition;

FIG. 10 is a perspective view of the actuation sled shown in FIG. 9 in a formed condition with the knife blade separated therefrom for illustrative purposes;

FIG. 11 is a perspective view of the formed actuation sled shown in FIG. 9 with the knife blade mounted to the blade support portion thereof;

FIG. 11A is a perspective view of the formed actuation sled of the disposable loading unit shown in FIG. 6A;

DETAILED DESCRIPTION OF PREFERRED EMBODIMENTS

Figure 2A:
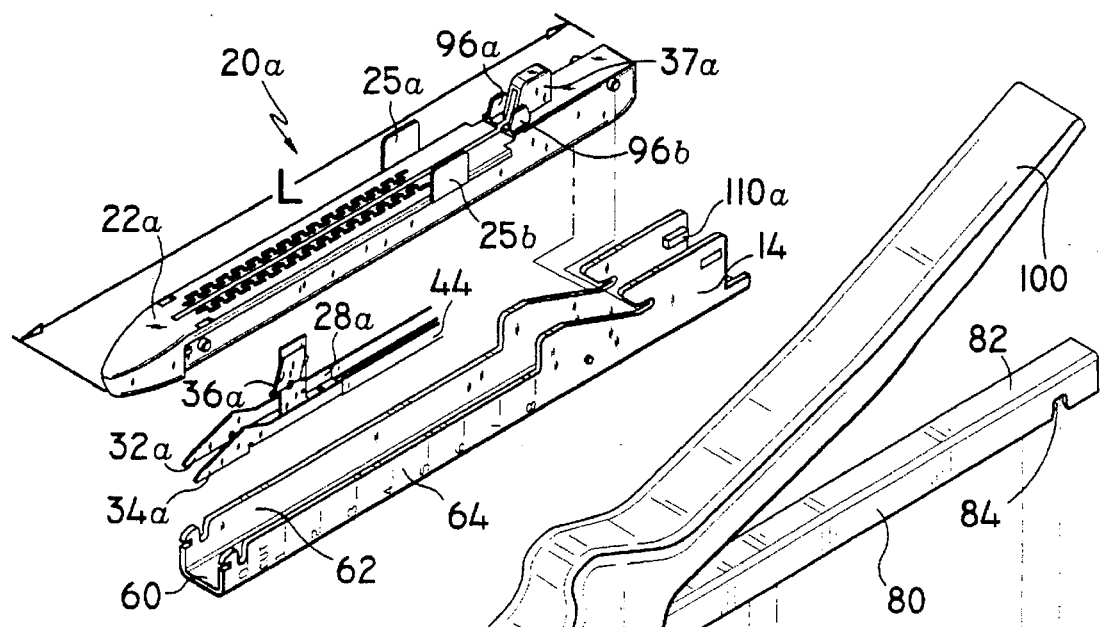
FIG. 2A is a perspective view of the cartridge retention channel of the surgical stapler illustrated in FIG. 2 illustrating the disposable loading unit shown in FIG. 1A.

In the drawings and in the description which follows, the term "proximal", as is traditional, will refer to the end of the apparatus which is closer to the operator, while the term "distal" will refer to the end of the apparatus which is further from the operator.

Referring now to the drawings wherein like reference numerals identify similar structural elements, there is illustrated in FIGS. 1 and 1A a surgical stapling device constructed in accordance with a preferred embodiment and designated generally by reference numeral 10 which includes a cartridge half section 11a and an anvil half section 11b. As will become readily apparent to those having ordinary skill in the art, surgical stapler 10 is constructed in such a manner so as to substantially reduce the costs associated with its fabrication and assembly as compared to prior art linear staplers. It will also become readily apparent that surgical stapler 10 is adapted to employ different sized disposable loading units. More particularly, in a preferred embodiment, surgical stapler 10 employs one loading unit which applies staple rows that are approximately 60 mm in length, designated by reference numeral 20a, and another loading unit which applies staple rows that are approximately 80 mm in length, designated by reference numeral 20. Thus, a single surgical stapler may be utilized to apply staple lines of varying length, which in the past, required two separate staplers. It should be understood that the stapler could be configured to receive loading units having staple line lengths other than those mentioned above and could also be configured to receive more than two different sized (i.e. staple line length) loading units.

Figure 2:
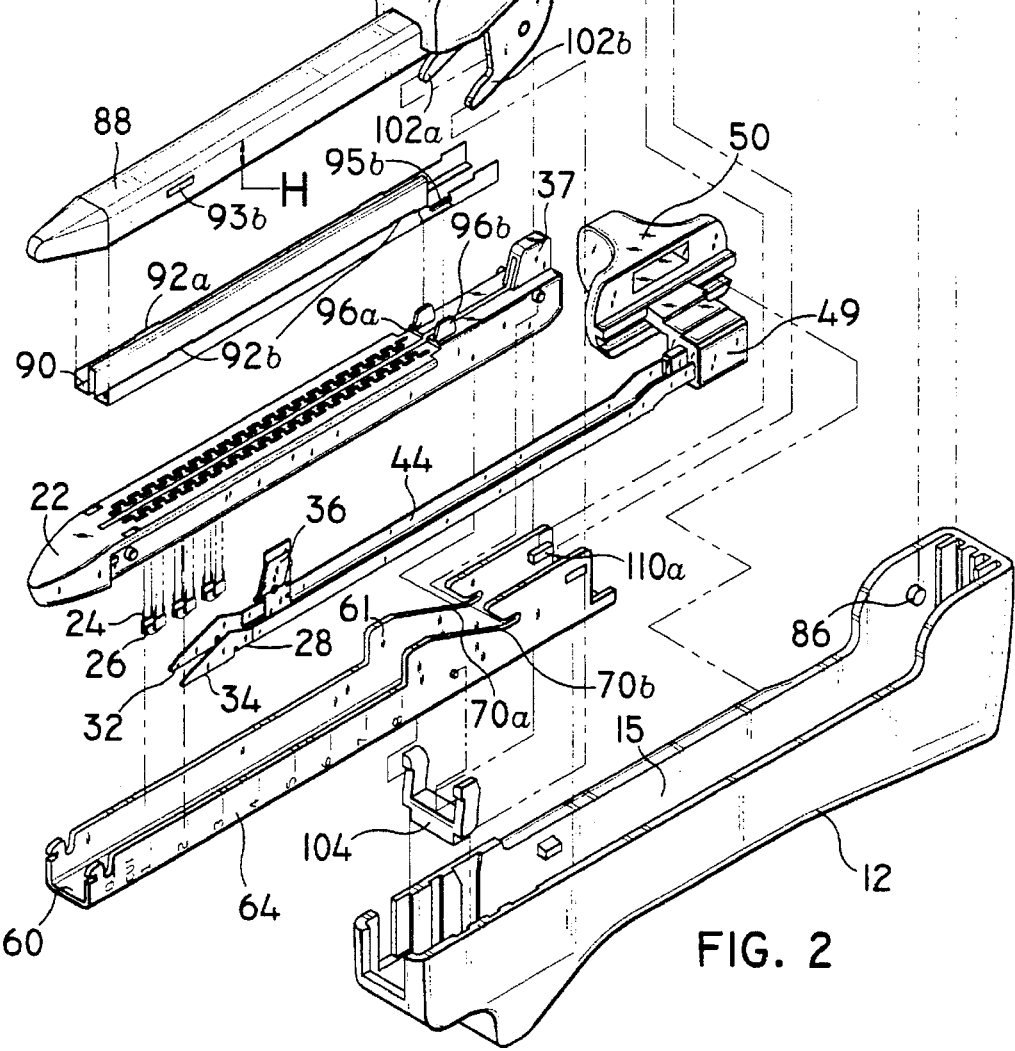
FIG. 2 is an exploded perspective view of the surgical stapling apparatus illustrated in FIG. 1.

Referring to FIGS. 2 and 3, surgical stapler 10 includes a body portion 12 defining a handle for grasping and supporting the device. A retaining channel 14 is mounted in the interior cavity 15 of body portion 12 adjacent the distal end thereof. Retaining channel 14 is dimensioned and configured to support disposable loading units 20 and 20A, as illustrated in FIGS. 3 and 3A.

Figure 6:
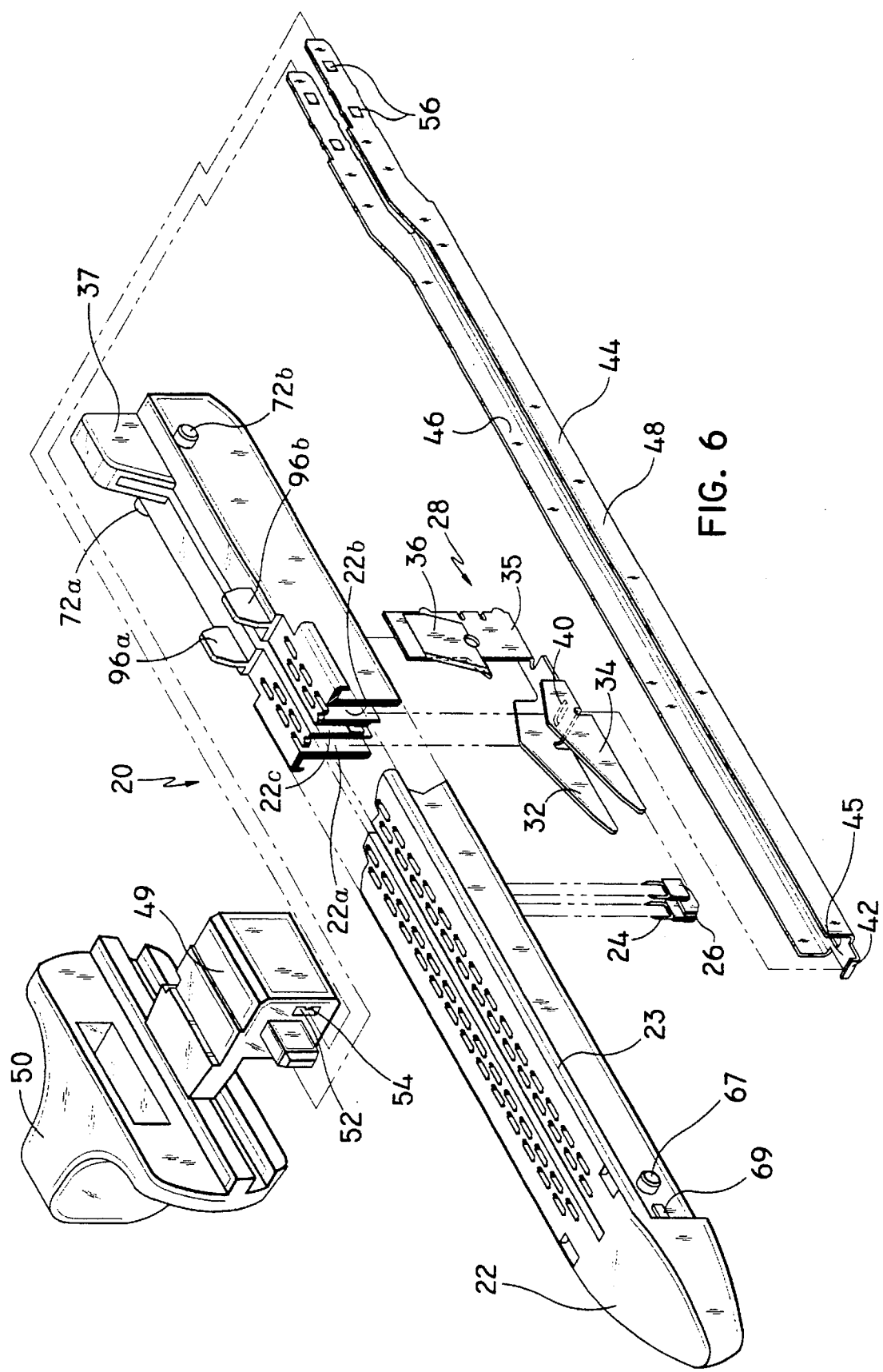
FIG. 6 is an enlarged exploded perspective view of the disposable loading unit and actuation assembly of the surgical stapling apparatus illustrated in FIG. 1.

As shown in FIG. 6, disposable loading unit 20 includes a cartridge 22 having a plurality of slots which support a corresponding number of surgical staples 24, a plurality of staple pushers or ejectors 26 adapted and configured to eject the staples from the slots when acted upon by a staple driving force, and an actuation sled 28 which is mounted to translate through cartridge 22 in a longitudinal direction to transmit a staple driving force to the ejectors. The cartridge is preferably composed of a liquid crystal polymer; although other materials of construction are contemplated. The cartridge has a lip 23 which engages the retention channel 14 to prevent inward rotation of the cartridge (see FIG. 6B).

As best seen in FIG. 9, actuation sled 28 is preferably monolithically formed from a single piece of sheet metal or a similar material which is folded into the desired structural configuration shown in FIG. 11. In this configuration, actuation sled (staple actuator) 28 defines a base portion 30, two upstanding cam wedges 32 and 34, and an upstanding shank 35 which supports a knife blade 36. Knife blade 36 is preferably spot welded to shank 35, although other known fastening methods may be employed. Also, the knife blade and shank can be one piece. As illustrated in FIG. 10, a weldment port 33 and a winglet 39 are provided to facilitate the proper alignment and cohesion of knife blade 36 to shank 35 during fabrication. Cam wedges 32 and 34 are staggered with respect to one another so that one leads the other throughout the sled's translation through cartridge 22. In doing so, the staple driving forces within cartridge 22 are reduced and become more balanced during a staple driving operation. Longitudinal slots 22a and 22b accommodate the longitudinal translation of cam wedges 32 and 34, while slot 22c accommodates the longitudinal translation of shank 35 (see FIG. 6). Although illustrated with a knife, it is also contemplated that the apparatus can be provided without a knife blade and therefore would staple tissue without making an incision.

The base portion 30 of actuation sled 28 has a transverse slot 40 defined therein which is dimensioned and configured to releasably retain an upturned flange 42 formed at the distal end of elongated actuation channel 44 (see FIG. 6). When the disposable loading unit 20 is placed into retaining channel 14 and actuation sled 28 is disposed in its proximal-most position, flange 42 releasably engages slot 40. Thus, movement of actuation channel 44 moves actuation sled 28. After a stapling operation, when the disposable loading unit is removed from the retaining channel, flange 42 is easily disengaged from slot 40.

With continued reference to FIG. 6, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam projects rearwardly to engage the mounting block 49 that is associated with firing knob 50. A pair of slots 52 (only one of which is shown) are formed in mounting block 49 for receiving the proximal end of each of the upstanding beams 46, 48 of actuation channel 44 and the slots are provided with detents 54 for engaging apertures 56 in the beam ends to lockingly retain the beams in mounting block 49. Alternately, a pair of slots can be formed through the bottom surface of mounting block 49 and the actuation channel can be U-shaped along its entire length with the proximal ends of beams 46 and 44 extending into the slots in an interference fit. In use, longitudinal movement of firing knob 50 causes corresponding longitudinal translation of actuation channel 44 and actuation sled 28.

Figure 6A:
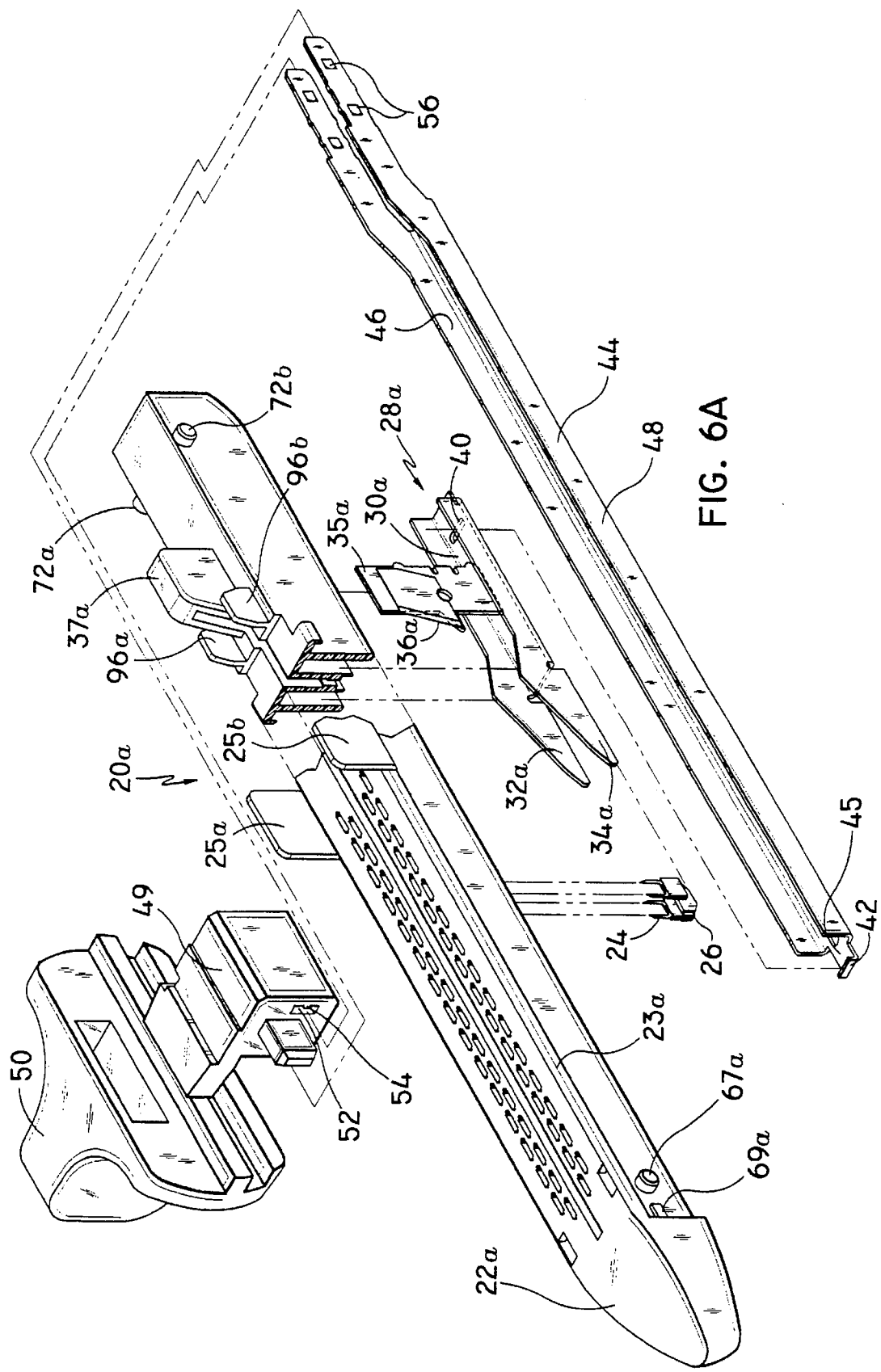
FIG. 6A is an enlarged exploded perspective view of the disposable loading unit and actuation assembly of the surgical stapling apparatus illustrated in FIG. 1A.
Figure 6B:
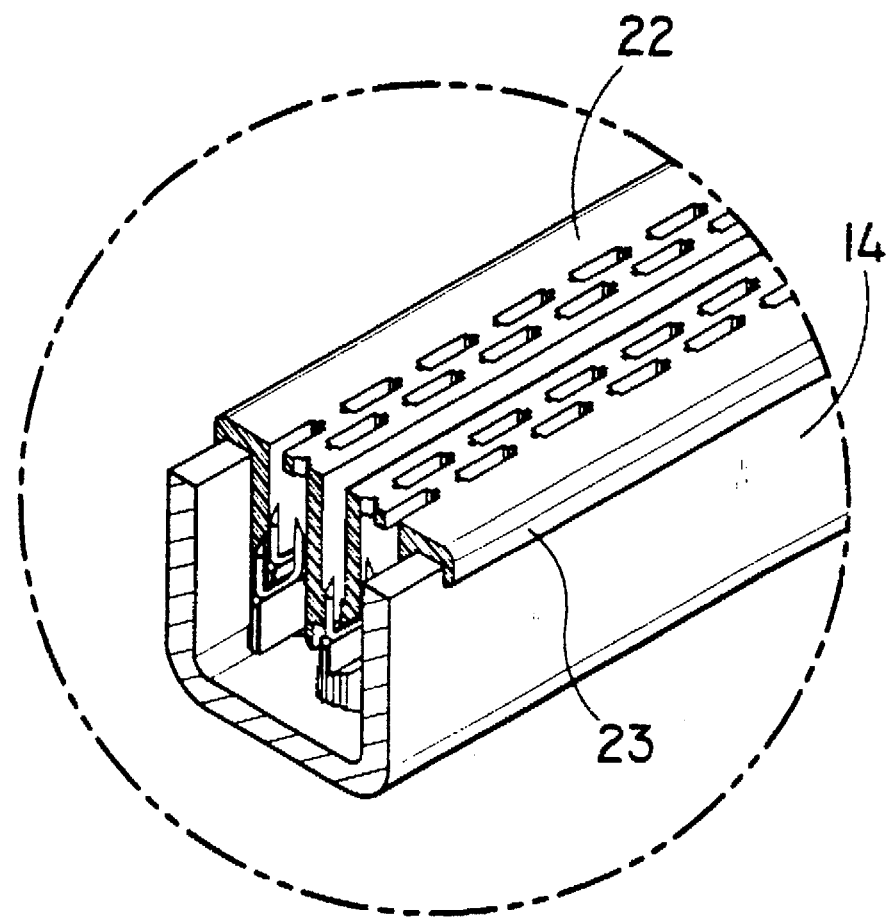
FIG. 6B is a cross-sectional view showing the engagement of the cartridge lip and the retention channel.

Turning now to FIG. 6A, disposable loading unit 20A is constructed in substantially the same manner as loading unit 20. However, loading unit 20A is preferably the same overall length L (FIG. 2A) as loading unit 20, and preferably about 5.61 inches. It includes a cartridge 22A which is dimensionally similar to cartridge 22 but which has fewer staple supporting slots formed therein. More particularly, several of the proximal staple slots formed in cartridge 20 are not provided in cartridge 20A (compare FIGS. 3 and 3A). In the exemplary embodiments, each staple line formed by cartridge 22A is approximately 60 mm in length, as compared to the 80 mm length of each staple line formed by cartridge 20. Thus, approximately 20 mm of each staple line provided in cartridge 22 is absent from cartridge 22A. To prevent body tissue from extending beyond the proximal end of each staple line provided in cartridge 22A, two lateral flanges 25a and 25b extend upwardly from the tissue contacting surface of the cartridge. As best seen in FIG. 1A, lateral flanges 25a and 25b are positioned beyond the lateral edges of the anvil half-section so as not to interfere with the approximation of the anvil half-section and cartridge half-section.

With continuing reference to FIG. 6A, loading unit 20A further includes actuation sled 28A which is substantially similar to the actuation sled 28 of loading unit 20. However, the base of actuation sled 28A is approximately 20 mm longer than that of actuation sled 28 to account for the 20 mm of "staple-less space" within cartridge 22A. Accordingly, when actuation sled 28A is in a prefired proximal position, actuation channel 44 is in the same longitudinal position as when sled 28 is employed (compare FIGS. 18 and 18A). Moreover, the dimensional differences between the two actuation sleds (compare FIGS. 11 and 11A) enable either loading unit 20 or 20A, which are of the same overall length, to be placed into retention channel 14 such that the distal flange 42 of actuation channel 44 engages either slot 40 or 40A without adjusting the longitudinal position of the actuation channel. Although the construction of actuation sled 28A substantially resembles that of actuation sled 28, because cam wedges 32A and 34A have proximal extensions, the sled must be fabricated in a slightly different manner. In particular, the upstanding shank 35A is preferably formed separate from the main structure and subsequently welded or affixed to the base 30A. The knife may be mounted to the shank before or after the shank is attached to the base.

Referring to FIGS. 2–2A, and 7–8, retention channel 14 includes a base portion 60 and two upstanding parallel walls 62 and 64. Numerical indicia is imprinted on the walls 62, 64 of the retention channel 14 to indicate the length of the staple line. Retention structures are provided at the distal end of each of the walls 62, 64 to engage corresponding structures provided on disposable loading units 20 and 20A. In particular, notches 66a and 66b are provided for engaging corresponding protuberances, such as protuberance 67 (protuberance 67A on cartridge 22A), and slots 68a and 68b are provided for engaging corresponding detents, such as detent 69 (detent 69A on cartridge 22A). These structures inhibit lateral, longitudinal and perpendicular shifting of cartridges 22 and 22A (and disposable loading units 20 and 20A as a whole) within retaining channel 14. Ramped engagement slots 70a and 70b are also defined in the opposed walls of retention channel 14 for interacting with a pair of opposed protuberances 72a and 72b, and 72A and 72B to guide disposable loading units 20 and 20A into retention channel 14 when loaded into surgical stapler 10 (see FIGS. 6 and 6A). Flanges 96a, 96b (and 96A, 96B) are spaced proximally of tissue stop portion 61 of retention channel 14. Portion 61 and the distal edge 13 of the handle portion, best seen in FIG. 3, cooperate to prevent tissue from extending proximally.

Referring again to FIG. 2, surgical stapler 10 further includes an elongate anvil support beam 80 which has a generally U-shaped cross-sectional configuration. Anvil support beam 80 and its associated structures are also referred to herein as the "anvil half-section". The distal end portion 88 of the anvil support beam 80 in one embodiment is tapered in height h in a distal direction to provide additional support and reduce deflection during a staple firing operation. Alternately, the height can remain constant. The proximal end portion 82 of support beam 80 has a notched area 84 for engaging a pair of corresponding detents 86 (only one of which is shown), which extend into the cavity 15 of body portion 12 adjacent the proximal end thereof. The detents 86 are engaged when the cartridge half-section 11a and anvil half-section 11b are mated with one another. The distal end portion 88 of anvil support beam 80 is configured to support a preformed anvil plate 90 against which staples are driven and formed during a stapling procedure.

Figure 12:
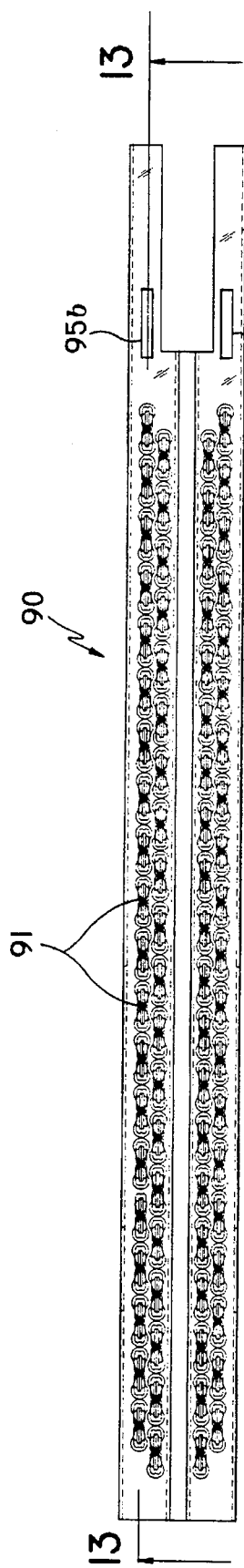
FIG. 12 is a plan view of the preformed anvil plate which is mounted to the anvil support beam of the upper body portion of the stapling apparatus shown in FIGS. 1 and 1A.
Figure 13:
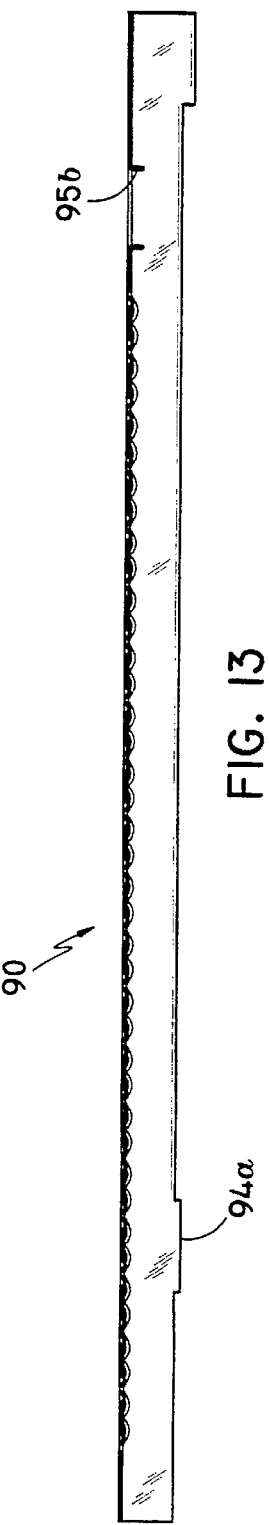
FIG. 13 is a cross-sectional view of the preformed anvil plate taken along line 13—13 of FIG. 12.
Figure 14:
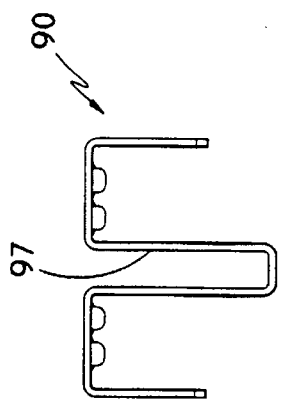
FIG. 14 is a front end view of the preformed anvil plate illustrated in FIGS. 12 and 13.

Referring to FIGS. 12 and 13, anvil plate 90 is formed from a unitary piece of metal and is cold formed and stamped to define a plurality of staple forming recesses or cups 91. Each staple forming recess corresponds to a particular staple housed within cartridge 22 (as well as cartridge 22A). Anvil plate 90, as shown in FIG. 2, has two pairs of opposed tangs 92a and 92b formed therein which extend inwardly to engage complementary engagement slots 93b (only one is shown) in anvil support beam 80 during fabrication and assembly (see FIG. 5). The cross-sectional configuration of anvil plate 90 is dimensioned to complement the cross-sectional geometry of support beam 80 (see FIG. 14). More particularly, the cavity 97 which extends along the length of the anvil plate 90 corresponds to a similar channel formed in support beam 80. These areas accommodate shank 35 and knife blade 36 (or shank 35A and knife blade 36A on actuation sled 28A) as the knife translates distally to form an incision in stapled body tissue during a stapling operation.

A pair of rectangular apertures 95a and 95b are formed in anvil plate 90 adjacent the proximal end thereof for receiving a pair of correspondingly positioned flanges 96a and 96b, and 96A and 96B which project upwardly away from the tissue contacting surfaces of cartridges 22 and cartridge 22A, respectively (see FIGS. 2 and 2A). The interaction between the apertures and flanges ensures that cartridges 22 and 22A and the anvil plate 90 are properly aligned (front to back) with one another during stapling procedures.

Referring again to FIG. 2, the anvil half-section of surgical stapler 10 further includes clamping handle 100 which is used to securely clamp tissue between the staple forming surface of anvil plate 90 and the tissue contacting surfaces of either cartridge 22 or cartridge 22A. Clamping handle 100 is pivotably mounted to anvil support beam 80 about a transverse pivot pin which is not shown in the drawings. A pair of clamping hooks 102a and 102b depend from clamping handle 100 for interacting with the U-shaped clamping beam 104 supported within the internal cavity defined in handle portion 12.

When stapler 10 is assembled prior to use, the notched area 84 at the proximal end 82 of anvil support beam 80 is engaged with the cooperating detents 86 in the inner cavity 15 of body portion 12. Thereupon, the anvil haf-section is mated with the cartridge half-section, and clamping handle 100 is disposed in the upright unclamped position shown in FIG. 1. Subsequently, when body tissue is properly disposed between the staple forming surface of anvil plate 90 and the tissue contacting surface of either cartridge, the anvil half section is pivoted toward the cartridge half section, about the detents in body portion 12, such that the distal ends of clamping hooks 102a and 102b are positioned immediately adjacent the proximal end of the base of U-shaped clamping beam 104. Concomitantly, flanges 96a and 96b (or 96A and 96B) engage apertures 95a and 95b in anvil plate 90 to ensure proper alignment (front to back) of the anvil and the cartridge.

Then, to securely clamp the captured body tissue, clamping handle 100 is pivoted from the position illustrated in FIG. 1 to that which is shown in FIG. 1A. At such a time, clamping hooks 102a and 102b engage the base of clamping beam 104, locking the stapler in a clamped condition. During clamping, the captured body tissue exerts a counter-force against the tissue contacting surface of cartridge 22 (or cartridge 22A) and the fastener forming surface of the anvil plate 90, urging the two structures apart. To overcome these forces and prevent the proximal portion 82 of anvil support beam 80 from bending, bearing surfaces are defined within the retention channel 14 to support the compressive forces generated during clamping. In particular, as illustrated in FIG. 7, opposed bearing shelves 110a and 110b are stamp formed in the opposed walls 62 and 64 of retention channel 14. The bearing shelves are positioned to abut the medial section of anvil support beam 80 proximate the clamping handle pivot point.

Figure 15:
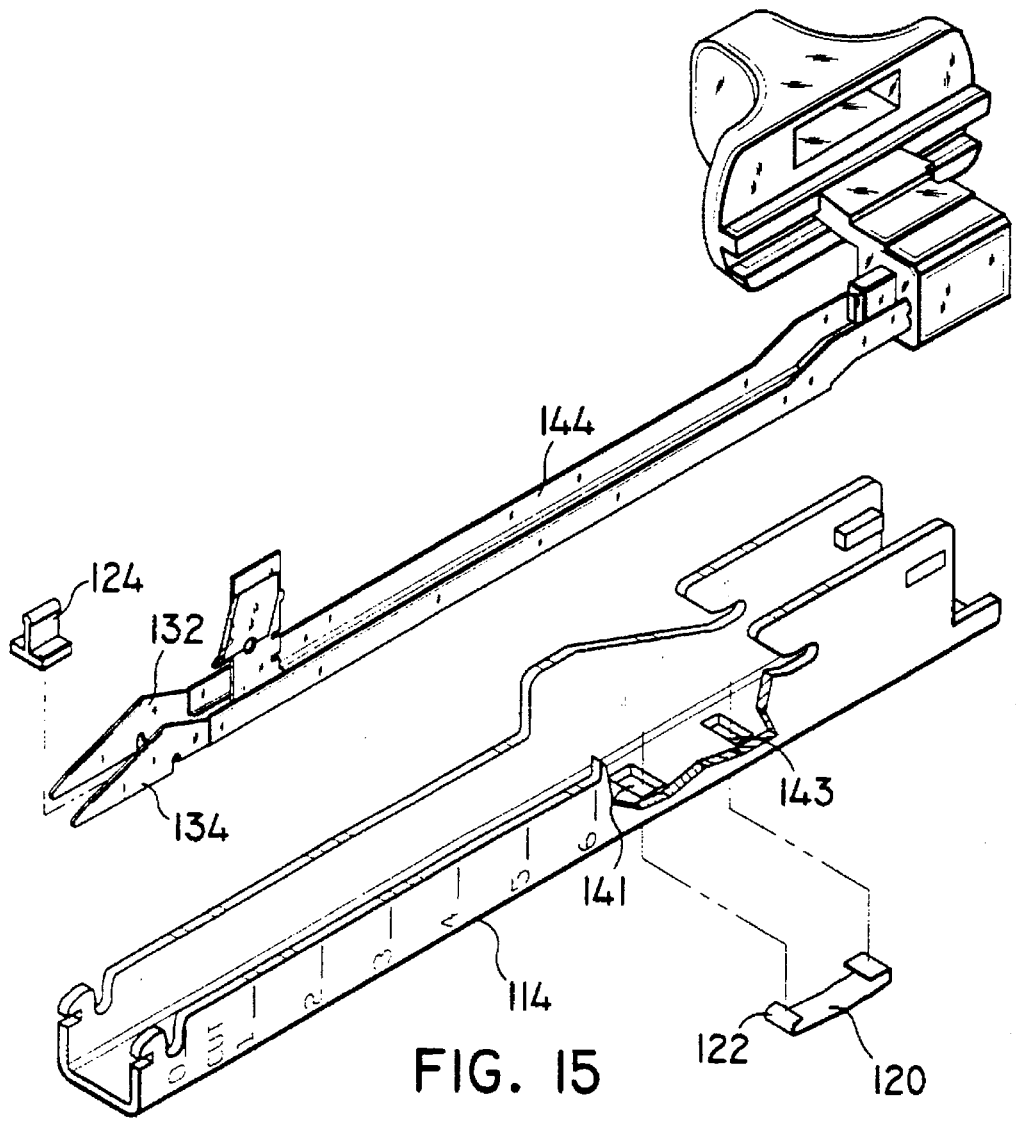
FIG. 15 is an exploded perspective view of an embodiment utilizing a lockout mechanism to prevent reactuation of the apparatus.
Figure 15A:
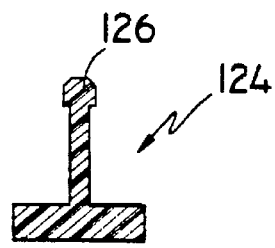
FIG. 15A is an enlarged cross-sectional view of the T-shaped member of the lockout mechanism.
Figure 16:
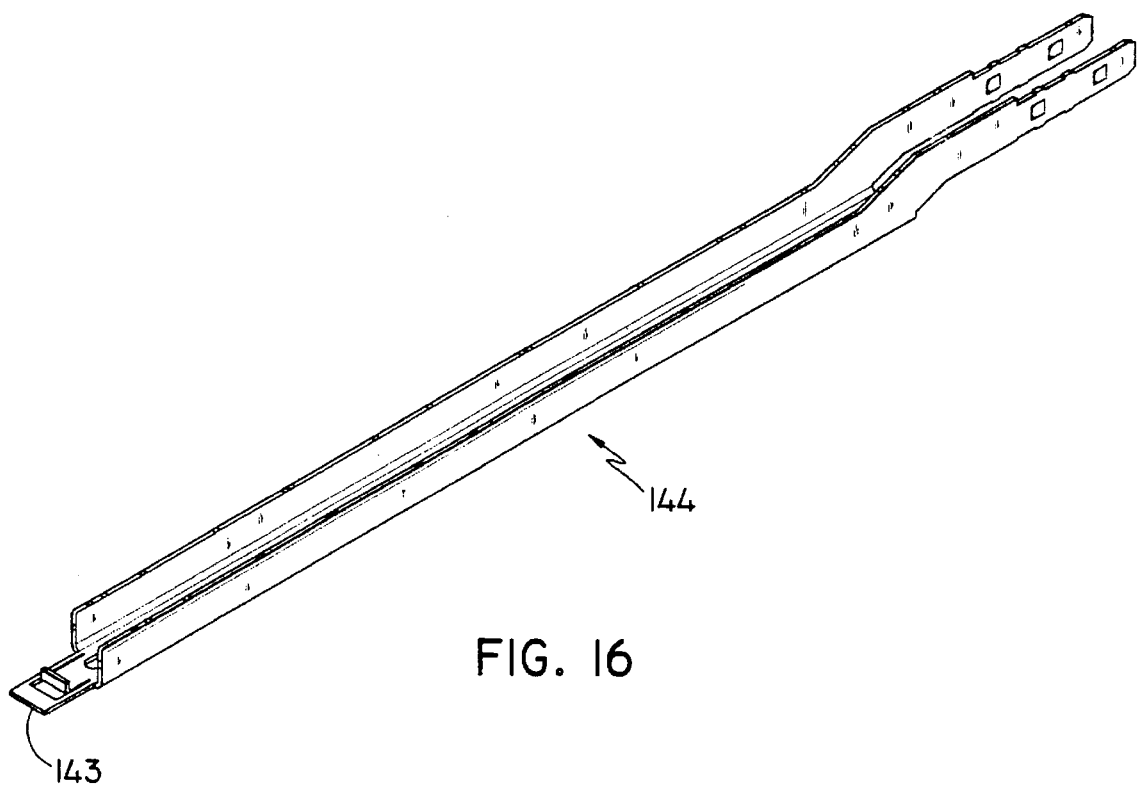
FIG. 16 is an enlarged perspective view of the actuation channel having an edge for engagement by the hook of the lockout mechanism.

It may also be desirable to provide a locking mechanism to prevent reactuation of the apparatus after it has been actuated. For example, a locking member 120 shown in FIG. 15 can be positioned in the retaining channel 114. The locking member 120 is biased to an upward engagement position and each end extends through a window 141, 143 in the channel 114. A T-shaped member 124 is positioned between the cam wedges 132, 134 to bias the hook portion 122 out of engagement with the actuation channel 144. Head portion 126 of T-shaped member 124 (FIG. 15A) is initially retained in the cartridge by a pair of detents in the cartridge which extend into the knife slot. When the stapler is actuated, head portion 126 of T-shaped member 124 rides in the knife slot. A second pair of detents at the distal end of the knife slot engages head portion 126 of T-shaped member 124 to hold it at the distal end of cartridge 122 when the cam wedges 132, 134 are advanced to the distal position. When actuation channel 144 is retracted from the post-actuated position to the pre-actuated position, the T-shaped member 124 remains forward allowing hook portion 122 to return to the upward position and extend through the window 141 in retaining channel 114 to engage edge 143 (FIG. 16) of actuation channel 144 to prevent advancement of the actuation channel. FIGS. 17A, 17B illustrate movement of the locking member 120 from an initial non-engaging position (FIG. 17A) out of engagement with actuation channel 144 to an engaging position (FIG. 17B) in engagement with actuation channel 144 to prevent distal movement thereof.

Figure 18:
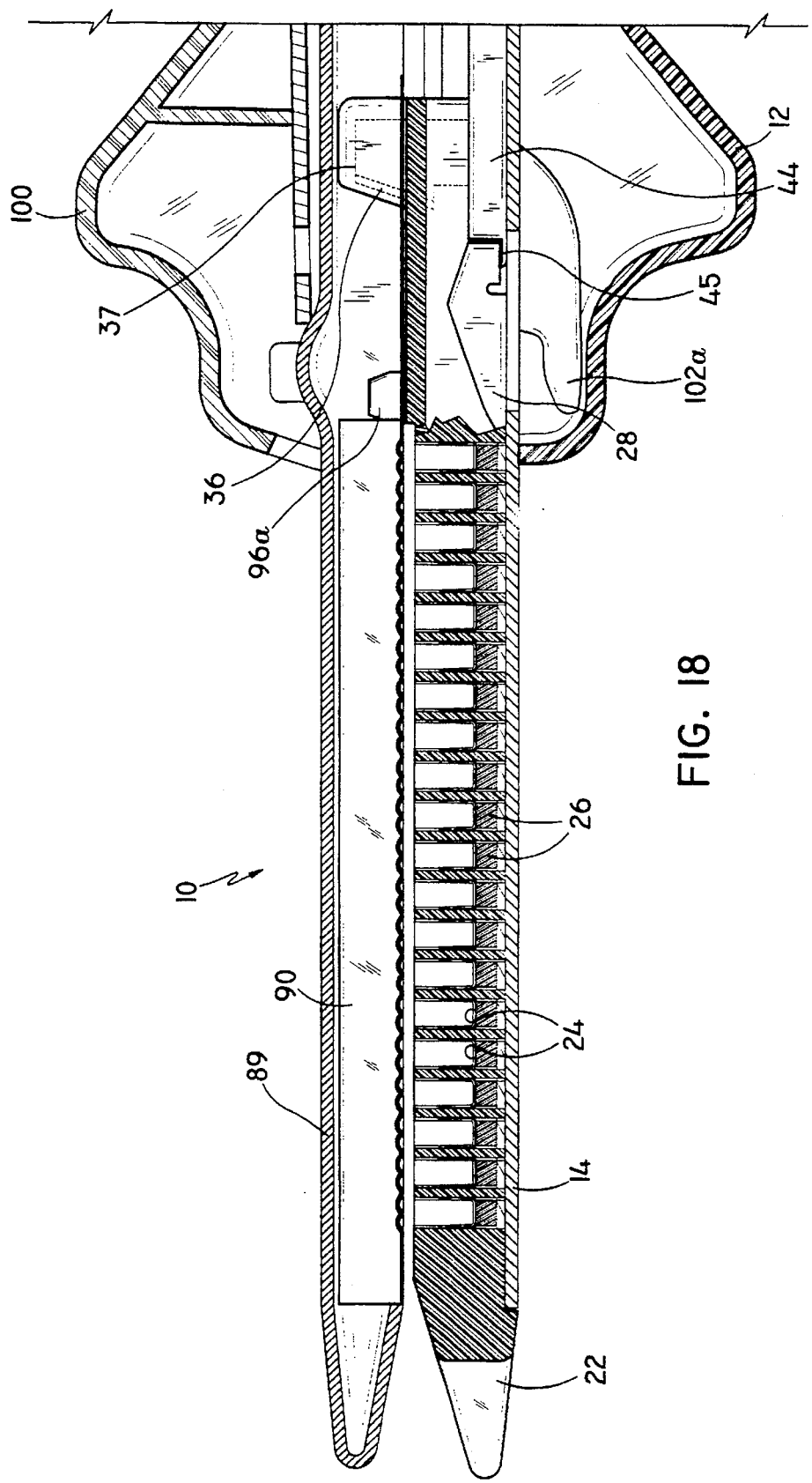
FIG. 18 is a side elevational view in cross-section of the surgical stapling apparatus with the actuation sled of FIG. 11 disposed in a pre-actuation proximal position.
Figure 18A:
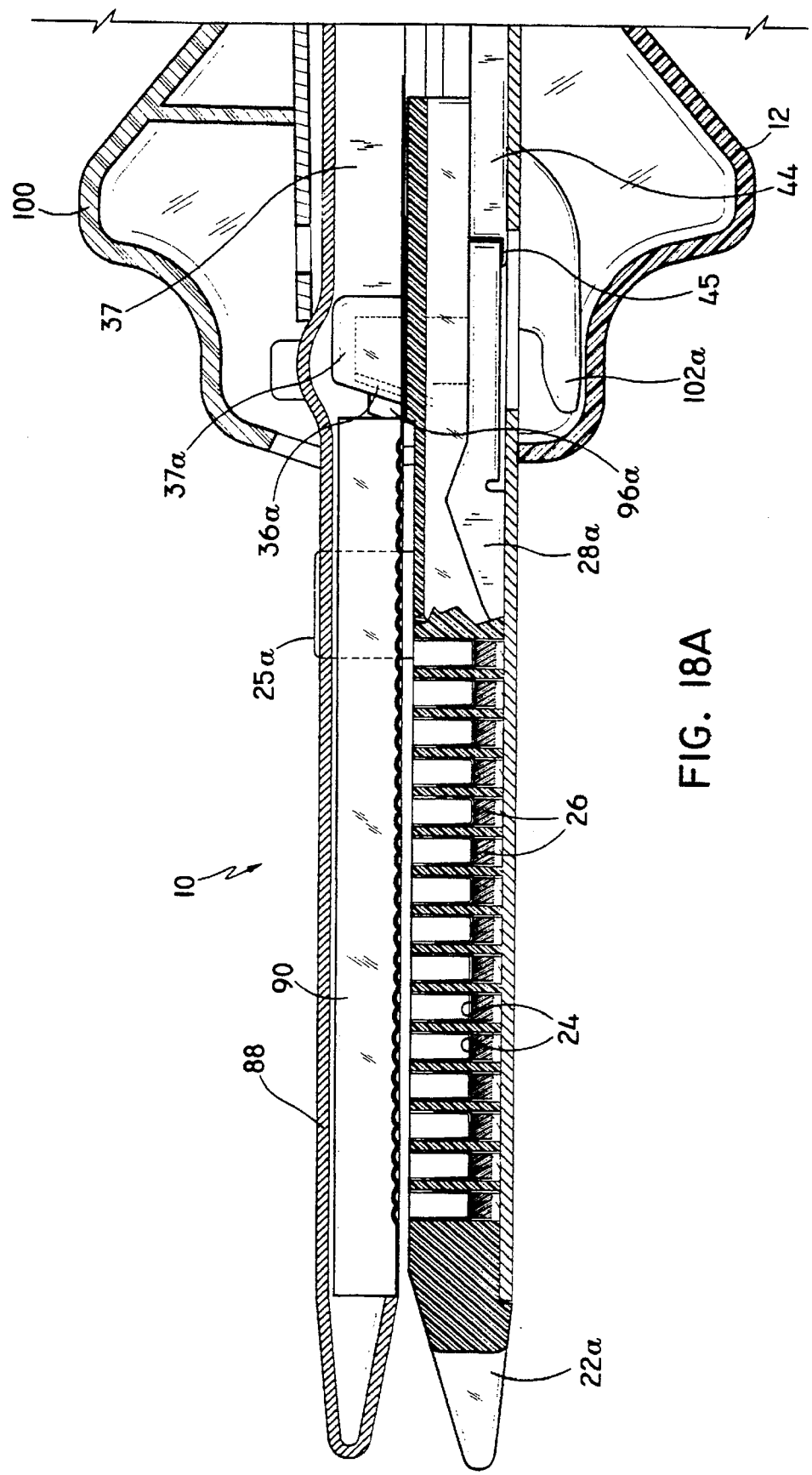
FIG. 18A is a side elevational view in cross-section of the surgical stapling apparatus of the subject application with the actuation sled of FIG. 11A disposed in a pre-actuation proximal position.
Figure 19:
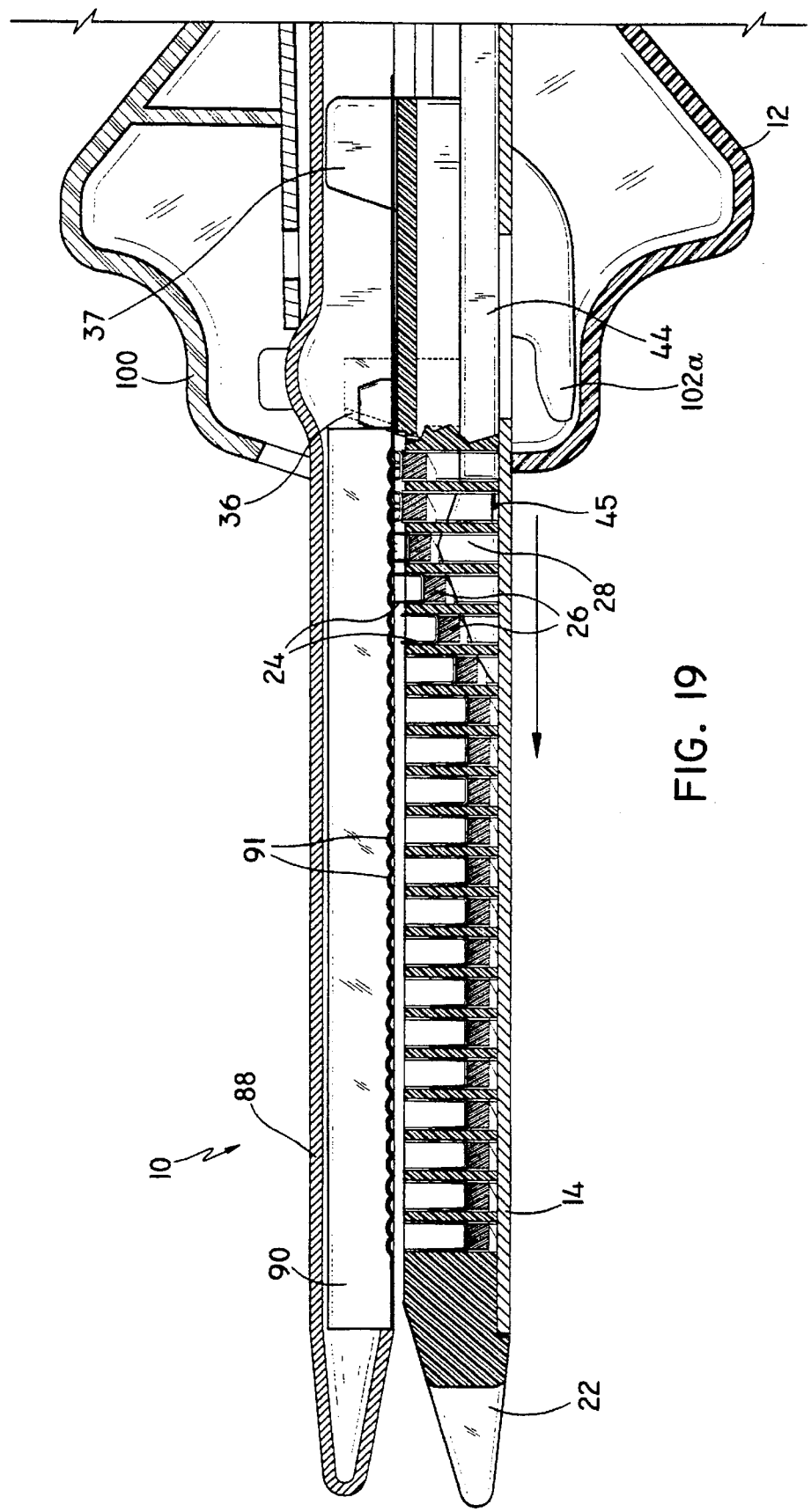
FIG. 19 is a side elevational view in cross-section of the surgical stapling apparatus of the subject application with the actuation sled of FIG. 11 disposed in a partially advanced position.
Figure 20:
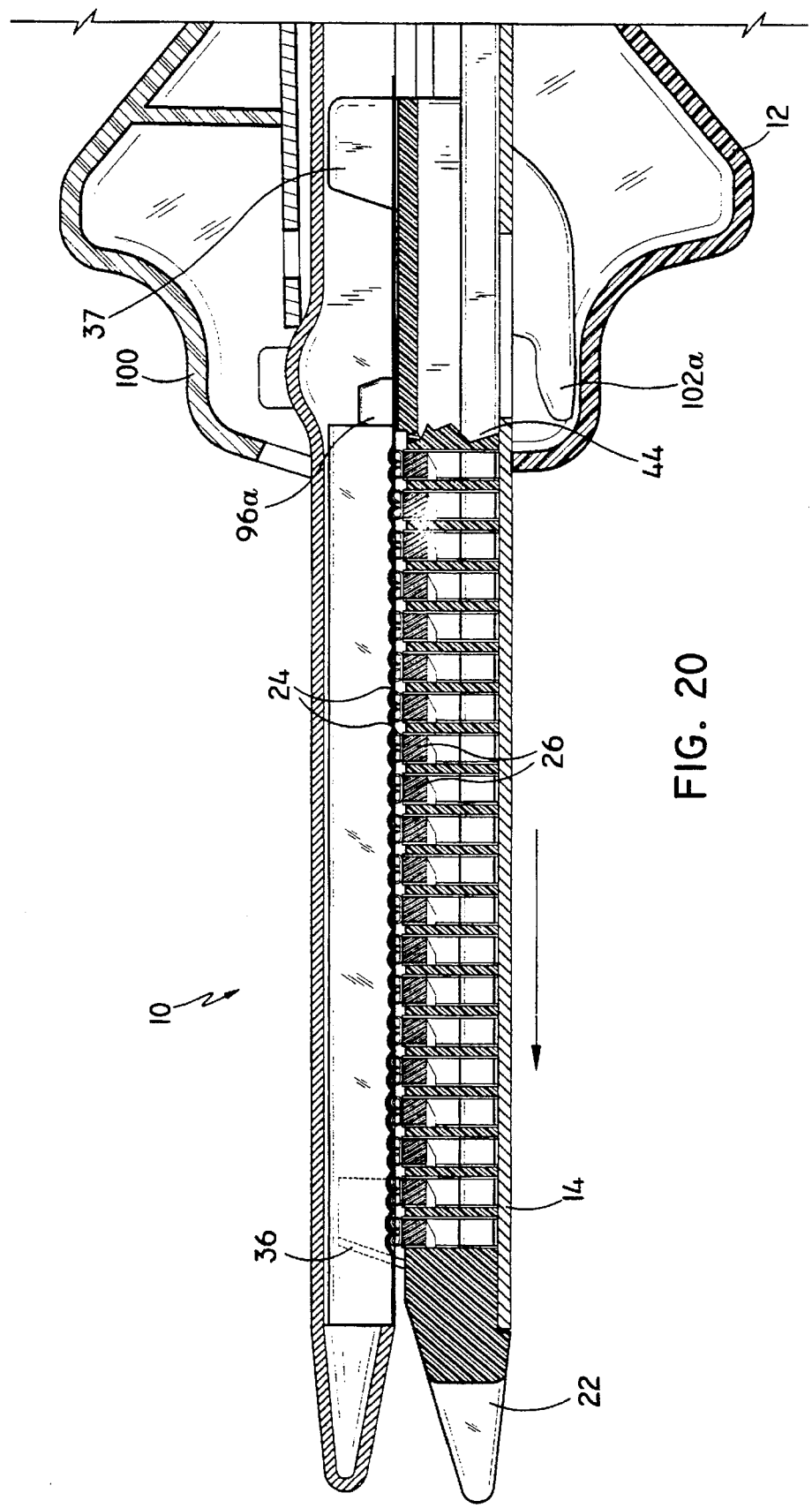
FIG. 20 is a side elevational view in cross-section of the surgical stapling apparatus of the subject application with the actuation sled of FIG. 11 advanced to the distal end of the cartridge.
Figure 21:
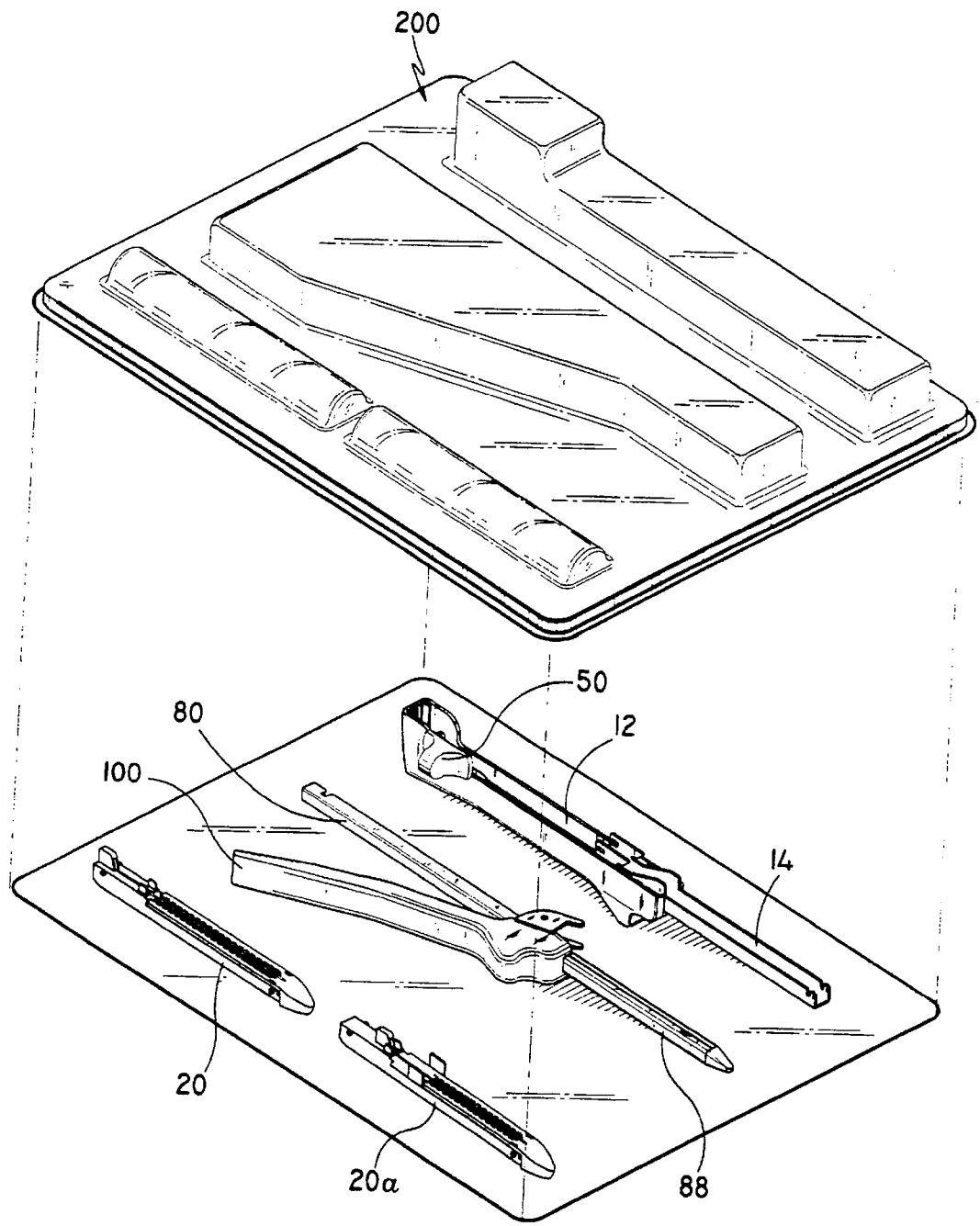
FIG. 21 is a perspective view of a kit which includes a surgical stapling apparatus constructed in accordance with a preferred embodiment and two different sized disposable loading units for use with the stapler.

Referring now to FIGS. 18–20 there is illustrated, in sequential order, a staple firing operation in which a plurality of staples are ejected from cartridge 22 (and in the case of FIG. 18A, from cartridge 22A) and driven against the staple forming surface of anvil plate 90. In operation, prior to firing surgical stapler 10, actuation sled 28 is in the proximal-most position shown in FIG. 18 (see also FIG. 18A). At such a time, knife blade 36 is enclosed in a protective housing 37 formed adjacent the proximal end of cartridge 22. (An identical housing structure 37A is provided on cartridge 22A to accommodate knife 36A). To fire the apparatus, firing knob 50 is moved in a distal direction. Accordingly, as illustrated in FIG. 19, actuation channel 44 drives actuation sled 28 into and distally through cartridge 22. During its distal translation, the angled leading surfaces of cam wedges 32 and 34 sequentially contact ejectors 26, urging them in a direction transverse to the direction of movement of actuation sled 28. As a result, the ejectors 26 push the staples 24 from their individual slots, driving each staple into a respective staple forming cup 91 in anvil plate 90. Knife blade 36 translates distally and forms an incision between the parallel rows of stapled body tissue as the staples are applied.

Figure 17:
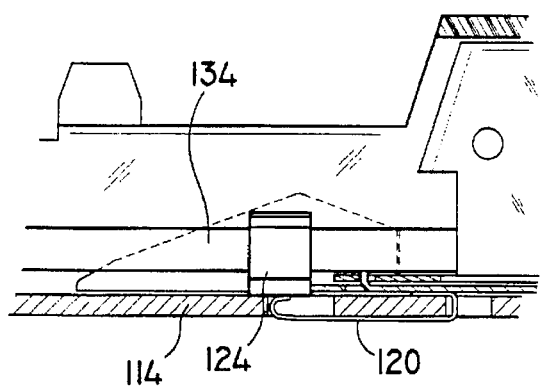
FIGS. 17 and 17A are side views of the lockout mechanism illustrating its movement from a non-engaging to an engaging position.
Figure 17A:
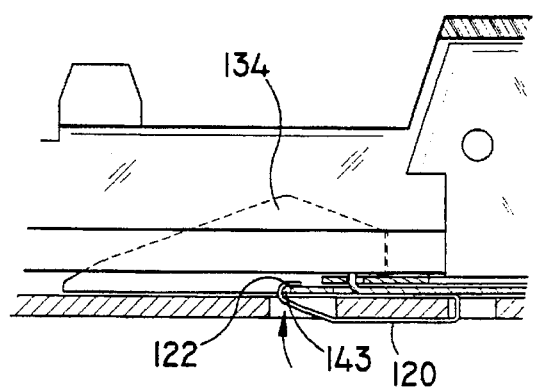

Sequential firing of the staples continues until actuation sled 28 is advanced to the distal end of cartridge 22, at which time, all of the staples once housed within the cartridge 22 will have been ejected (see FIG. 17). The identical sequence of events occurs when loading unit 20A is disposed in retaining channel 14. After a stapling procedure, the firing knob 50 is retracted to its original position, the cartridge and anvil sections are separated, and the spent disposable loading unit is removed from retaining channel 14. Subsequently, a new, fully loaded disposable loading unit can be positioned in retaining channel 14 such that the slot 40 of the actuation sled 28 (or sled 28A) engages the flange 42 of actuation channel 44 to enable re-use of the apparatus.

As is apparent, the stapler 10 described herein can accommodate disposable loading units having staple arrays of varying lengths, thereby reducing costs by enabling a single stapler to be used rather than a separate stapler for each size loading unit. It is also more convenient for the user to be able to load various sized loading units into a single stapler instead of having to match the particular loading unit with the specified stapler.

Referring now to FIG. 20, surgical stapler 10 and interchangeable disposable loading units 20 and 20A can be provided as a set or kit marketed in a packaging unit defined by a hermetically sealable molded plastic container which is designated generally by reference numeral 200 and enables ready access to the disposable loading units. Container 200 is one example of a kit and is formed with several recessed areas shaped to accommodate the anvil and cartridge half-sections of surgical stapler 10, and the two disposable loading units 20 an 20A employed therewith. The stapler could alternately be packaged with a loading unit mounted therein and the half sections mated. As noted hereinabove, loading unit 20 facilitates the sequential application of parallel rows of staples of a length greater than the length of staple rows of loading unit 20a. For example, loading unit 20 staple line can measure approximately 60 mm in length, and loading unit 20A staple line can measure approximately 80 mm in length. Thus, the user can insert the appropriate sized disposable loading unit during the procedure into the same stapler housing, thus reducing costs compared to the use of two separate staplers. It is also contemplated that additional loading units could be included in the kit. Alternately, the loading unit themselves can be packaged and sold separately from the stapler (either individually or with other disposable loading units) for use with the stapler which would also reduce costs since the user would need to stock only one instrument for accommodating disposable loading units of different sizes. The loading units can be of the same or different sized staple lengths than those described above.

Although the stapler 10 is shown and described above as being disposable, it is also contemplated that the stapler could be re-usable and resterilized after each procedure. The disposable loading units would then be offered separately for use with the re-usable stapler.

Although the subject apparatus has been described with respect to preferred embodiments, it will be readily apparent to those having ordinary skill in the art to which it appertains that changes and modifications may be made thereto without departing from the spirit or scope of the subject apparatus as defined by the appended claims.

What is claimed is:

1. A surgical stapling kit which comprises:
   a) a surgical stapler including:
      i) a first body portion supporting an anvil which defines a fastener forming surface; and
      ii) a second body portion configured to releasably mate with the first body portion and having a retention channel extending from a distal end thereof;
   b) a first disposable loading unit configured to be removably supported in the retention channel and including a cartridge carrying a plurality of staples arranged in at least two parallel rows which form staple lines having a first lengthwise dimension; and
   c) a second disposable loading unit configured to be removably supported in the retention channel and including a cartridge carrying a plurality of staples arranged in at least two parallel rows which, when applied to body tissue, form staple lines having a second lengthwise dimension different from the first lengthwise dimension of the staple lines formed by the first loading unit.

2. A surgical stapling kit as recited in claim 1, wherein the lengthwise dimension of the staple lines associated with the first loading unit is greater than the lengthwise dimension of the staple lines associated with the second loading unit.

3. A surgical stapling kit as recited in claim 2, wherein the lengthwise dimension of the staple lines associated with the first loading unit is approximately 80 mm and the lengthwise dimension of the staple lines associated with the second loading unit is approximately 60 mm.

4. A surgical stapling kit as recited in claim 2, wherein the second disposable loading unit includes a pair of lateral flanges extending from a tissue contacting surface to form a tissue stop.

5. A surgical stapling kit as recited in claim 4, wherein the flanges project from lateral edges of the tissue contacting surface thereof adjacent a proximal end of the staple rows to form a tissue stop structure.

6. A surgical stapling kit as recited in claim 1, wherein each loading unit includes an actuation sled which translates through the cartridge in a longitudinal direction to sequentially eject the staples therefrom and drive the staples against the fastener forming surface of the anvil.

7. A surgical stapling kit as recited in claim 6, wherein the actuation sled supported in the second loading unit has a lengthwise dimension which is greater than that of the actuation sled supported in the first loading unit.

8. A surgical stapling kit as recited in claim 7, wherein the surgical stapler further includes an elongate actuation shaft mounted for longitudinal translation within the second body portion and having an upturned flange at a distal end thereof for releasably engaging a complementary slot formed in the actuation sled supported within either the first or second disposable loading unit.

9. A surgical stapling kit as recited in claim 8, wherein the surgical stapler further includes a firing knob connected to a proximal end portion of the actuation shaft for effectuating the longitudinal translation thereof.

10. A surgical stapling kit as recited in claim 6, wherein each loading unit includes a pair of spaced apart upstanding posterior flanges projecting from a tissue contacting surface thereof, adjacent a proximal end of the tissue contacting surface, to engage a pair of corresponding apertures formed in a proximal portion of the anvil when the first and second body portions are mated with one another.

11. A surgical stapling kit as recited in claim 4, wherein the lengthwise dimension of the staple lines associated with the first loading unit is greater than the lengthwise dimension of the staple lines associated with the second loading unit and the actuation sled supported in the second loading unit has a lengthwise dimension which is greater than a lengthwise dimension of the actuation sled supported in the first loading unit.

12. A surgical stapling kit as recited in claim 1, wherein each loading unit includes engagement structures for engaging complementary engagement structures provided within the retention channel of the second body portion to releasably secure the loading units therein.

13. A surgical stapling kit as recited in claim 1, further comprising an enclosure for retaining the first and second body portions of the surgical stapler and the first and second disposable loading units associated therewith in a readily accessible manner.

14. A surgical stapling kit as recited in claim 1, wherein the overall length of the second disposable loading unit is substantially equal to the overall length of the first disposable loading unit.

15. A surgical stapling kit which comprises:
a) a first disposable loading unit configured to be removably supported in a retention channel of a surgical stapler and including:
1) a cartridge carrying a plurality of staples arranged in at least two parallel rows which form staple lines having a first lengthwise dimension; and
2) a wedged actuation sled mounted to translate through the staple housing in a longitudinal direction to effectuate sequential ejection of the staples therefrom; and
b) a second disposable loading unit configured to be removably supported in the retention channel of the surgical stapler and including:
1) a cartridge carrying a plurality of staples arranged in at least two parallel rows which form staple lines having a second lengthwise dimension different from the first lengthwise dimension of the staple lines formed by the first loading unit; and 2) a wedged actuation sled mounted to translate through the staple housing in a longitudinal direction to effectuate sequential ejection of the staples therefrom.

16. A surgical stapling kit as recited in claim 15, wherein the lengthwise dimension of the staple lines associated with the first loading unit is greater than the lengthwise dimension of the staple lines associated with the second loading unit.

17. A surgical stapling kit as recited in claim 16, wherein the overall length of the first loading unit is substantially equal to the overall length of the second loading unit.

18. A surgical stapling kit as recited in claim 16, wherein the actuation sled supported in the second loading unit has a lengthwise dimension which is greater than that of the actuation sled supported in the first loading unit.

19. A surgical stapling kit as recited in claim 18, wherein the overall length of the first loading unit is substantially equal to the overall length of the second loading unit.

20. A surgical stapling kit as recited in claim 15, wherein each cartridge supports a plurality of staple pushers positioned adjacent the staples supported therein, the pushers interacting with the wedged actuation sled during the longitudinal translation thereof to drive the staples from the staple housing toward the staple forming surface of the anvil.

21. A surgical stapling apparatus comprising:
a) a first body portion supporting an anvil which defines a fastener forming surface;
b) a second body portion having a retention channel extending from a distal end thereof, the second body portion having an actuator supported therein for movement between a first position and a second position;
c) a first disposable loading unit supported in the retention channel and including a plurality of staples arranged in at least two parallel rows which form staple lines having a first lengthwise dimension and a plurality of staple drivers movable in a direction transverse to the direction of movement of the actuator to apply the staples to body tissue, the disposable loading unit being removable and replaceable with a second disposable loading unit having a plurality of staples arranged in at least two parallel rows which form staple lines having a second lengthwise dimension different than the first lengthwise dimension of the staple lines of the first disposable loading unit.

22. A surgical stapling apparatus as recited in claim 21, wherein the first disposable unit has a first overall length and is replaceable with the second disposable unit having a second overall length substantially equal to the first overall length.

23. A surgical stapling apparatus as recited in claim 22, wherein the first disposable loading unit has an actuation member disposed therein having a first length and movable in a distal direction for firing the staples, the first disposable loading unit being replaceable with the second disposable loading unit having an actuation member having a second length different from the first length of the actuation member of the first disposable loading unit.

* * * * *